United States Patent [19]

Kupper

[11] Patent Number: 5,560,913

[45] Date of Patent: Oct. 1, 1996

[54] PHARMACEUTICAL COMPOSITIONS

[75] Inventor: Philip L. Kupper, Cincinnati, Ohio

[73] Assignee: The Procter & Gamble Company, Cincinnati, Ohio

[21] Appl. No.: 379,407

[22] Filed: Jan. 27, 1995

[51] Int. Cl.[6] .................... A61K 35/78; A61K 31/44; A61K 31/19

[52] U.S. Cl. .................. 424/195.1; 514/289; 514/357; 514/568; 514/653; 514/819; 514/820; 514/825; 514/849; 514/853; 514/855; 514/858; 514/859; 514/461; 514/885; 514/893

[58] Field of Search ................... 424/195.1; 514/819, 514/820, 829, 849, 853, 855, 859, 858, 861, 863, 885, 289, 357, 568, 653

[56] References Cited

U.S. PATENT DOCUMENTS

| | | | |
|---|---|---|---|
| 3,892,853 | 7/1975 | Cobble | 424/195 |
| 3,920,816 | 11/1975 | Seegall et al. | 424/195 |
| 4,178,372 | 12/1979 | Coats | 424/195 |
| 4,572,832 | 2/1986 | Kigasawa et al. | 424/19 |
| 4,675,009 | 6/1987 | Hymes et al. | 604/304 |
| 4,686,211 | 8/1987 | Hara et al. | 514/148 |
| 4,735,935 | 4/1988 | McAnalley | 514/43 |
| 4,952,560 | 8/1990 | Kigasawa et al. | 514/2 |
| 4,959,214 | 9/1990 | McAnalley | 424/195.1 |
| 4,971,791 | 11/1990 | Tsau et al. | 424/81 |
| 5,073,366 | 12/1991 | Beck | 424/720 |
| 5,200,488 | 4/1993 | Nagase et al. | 528/28 |
| 5,234,957 | 8/1993 | Mantelle | 514/772.6 |
| 5,286,489 | 2/1994 | Tsau et al. | 424/440 |

FOREIGN PATENT DOCUMENTS

| | | | |
|---|---|---|---|
| 892207 | 2/1982 | Belgium . | |
| 2128447 | 6/1971 | Germany | A61K 27/14 |
| 4120991 | 6/1991 | Germany | A61K 31/70 |
| 2245143 | 1/1992 | United Kingdom | A61K 35/78 |

OTHER PUBLICATIONS

"Treatment of children with persistent cough and pharyngitis" Vestik Otorinolaringologii 0(4): 13–16.

"The Aloe Vera Phenomenon: A Review of the Properties and Modern Uses of the Leaf Parenchyma Gel", Grindlay/Reynolds Journal of Ethnopharmacology, 16 (1986) 117–151.

"Aloe" The Lawrence Review of Natural Products (1992).

"Prostaglins & Thromboxane", Heggers/Robson Critical Care Clinics, vol. 1, No. 1, Mar. 1985.

*The Honest Herbal A Sensible Guide to the Use of Herbs and Related Remedies*, Tyler, 1993, Haworth Press.

"Traditional Medicinal Plants of Saudi Arabia", Al–Said, American Journal of Chinese Medicine, vol. XXI, Nos. 3–4, pp. 291–298, 1993.

"Aloe Vera Gel in Peptic Ulcer Therapy: Preliminary report", Blitz/Smith/Gerard, Journal A.O.A., vol. 62, Apr. 1963.

*Traumatic Injury: Infection and other Immunologic Sequelae:* "Prostaglins and Thromboxanes", Heggers/Robson, University Park Press, 1983.

"Characterization of Aloe vera Gel before and after Autodegradtion, and Stabilization of the Natural Fresh Gel", Yaron, Phytotherapy Research, vol. 7, S11–S13 (1993).

"Dermaide Aloe/Aloe vera Gel: Comparison of the Antimicrobial Effects", Heggers/Pineless/Robson, J. Amer. Med. Technol., Sep.–Oct. 1979.

"Wound Healing Alterations Caused by Infection", Robson/Stenberg/Heggers, Clinics in Plastic Surgery, vol. 17, No. 3, Jul. 1990.

"Prostanoid Derivatives in Thermal Injury", Boswick, Jr., The Art and Science of Burn Care pp. 275–283.

"Two Functionally and Chemically Distinct Immunomodulatory Compounds in the Gel of Aloe Vera", Hart/vanEnckevort/Dijk/Zaat/de Silva/Labadie, Journal of Ethnopharmacology, 23 (1988) 61–71.

"Aloe vera as a Biologically Active Vehicle for Hydrocortisone Acetate":; Davis/Parker/Murdoch, Journal of the American Podiatric Medical Association, vol. 81, No. 1, Jan. 1991.

"Aloe vera and Wound Healing", Davis/kabbani/Maro, Journal of the American Podiatric Medical Association, vol. 77, No. 4, Apr. 1987.

"The Therapeutic Efficacy of Aloe vera Cream in Thermal Injuries: Two Case Reports", Cera/Heggers/Robson/Hagstrom, Journal of the American Animal Hospital Association, Vo. 16, Sep./Oct. 1980, pp. 768–772.

"Bacterial and Wound–Healing Properties of Sodium Hypochlorite Solutions: The 1991 Lindberg Award", Heggers/Sazy/Stenberg/Strock/McCauley/Herndon/Robson, *Journal of Burn Care & Rehabilitation*, vol. 12, No. 5, pp. 420–424, Sep. 1991.

"Effect of Orally Consumed Aloe Vera Juice on Gastrointestinal Function in Normal Humans", Bland, Preventative Medicine, Mar./Apr. 1985.

Aloecorp–Technical Reference.

Aloecorp Material Safety Data Sheet, Aloe Vera Gel 1:1.

Aloecorp Material Safety Data Sheet, Aloe Vera Spray Dried Powder 100:1.

Aloecorp Material Safety Data Sheet, Aloe Vera Freeze Dried Powder 200:1.

*Primary Examiner*—John W. Rollins
*Attorney, Agent, or Firm*—Douglas C. Mohl; Jacobus C. Rasser; David K. Dabbiere

[57] ABSTRACT

The present invention relates to orally ingestible, pharmaceutical compositions containing at least one pharmaceutical active and a taste masking component.

16 Claims, No Drawings

1

PHARMACEUTICAL COMPOSITIONS

TECHNICAL FIELD

The present invention relates to orally ingestible, pharmaceutical compositions containing aloe vera as a taste masking agent.

BACKGROUND OF THE INVENTION

Individuals having difficulty swallowing tablets and capsules usually prefer chewable, quick-dissolving or liquid dosage forms. Oftentimes, however, the pharmaceutical actives incorporated into such dosage forms have a strong bitter taste. This is particularly true where pharmaceutical actives containing amine or amido groups or salts thereof are concerned. Aesthetic qualities such as taste and after-taste are important concerns for user acceptability. Products with poor flavor, bad after-taste or other negative aesthetics may limit overall user acceptability initially and over an extended period of time, eventually limit usage and compliance.

Sweeteners and flavors, along with various diluents, have been used as excipients or fillers in an attempt to minimize or mask such unpleasant or bitter tastes (or after-tastes). More recently, however, the focus has shifted to coating or structural matrix forms of taste masking. Compositions employing such technology have incorporated agents such as silicate clays, U.S. Pat. No. 3,140,978 and U.S. Pat. No. 4,581,232; acrylic acid copolymers, U.S. Pat. No. 5,286,489; gums, U.S. Pat. No. 5,288,500; and waxes in an effort to further provide improved tasting pharmaceutical compositions.

There still remains, however, a need for additional pharmaceutical compositions incorporating unpleasant tasting pharmaceutical actives which provide improved taste masking of the unpleasant tasting pharmaceutical active. The present inventor has discovered that the compositions of the present invention with at least one unpleasant tasting pharmaceutical active and which contain an aloe vera component provide improved tasting, orally administered, pharmaceutical compositions.

It is therefore an object of the present invention to provide improved tasting, oral compositions. It is a further object of the present invention to provide improved tasting compositions containing at least one pharmaceutically active ingredient. A still further object of the present invention is to provide a method of reducing or abating the symptoms associated with the common cold, respiratory disorders, gastrointestinal disorders and allergies using improved tasting compositions containing at least one pharmaceutically active ingredient. A still even further object of the present invention is to provide a method of making improved tasting, quick dissolving, freeze (or vacuum) dried compositions containing at least one pharmaceutically active ingredient.

SUMMARY OF THE INVENTION

The present invention relates to a pharmaceutical composition suitable for oral administration comprising:
 a) a safe and effective amount of at least one unpleasant tasting, pharmaceutical active; and
 b) an effective amount of an aloe vera component for taste masking the unpleasant tasting, pharmaceutical active wherein the aloe vera component contains no more than about 1% anthraquinones and wherein the ratio of pharmaceutical active to aloe vera component is at least 1.5:1.

By "safe and effective amount," as used herein, is an amount that is effective to mitigate and/or treat the symptoms for which the active ingredient is indicated in a human without undue adverse side effects commensurate with a reasonable risk/benefit ratio.

By the term "pharmaceutically acceptable oral carrier," as used herein, means a vehicle suitable for oral administration by ingestion in a safe and effective manner.

By the term "decolorized," as used herein, describes aloe vera products having undergone a single (or additional) filtration or extraction step to remove excess anthraquinone derivatives.

The pH of those compositions herein described range from about 3.5 to about 9.5, with the preferred pH being from about 4.0 to about 6.0 and the most preferred pH being 4.0 to about 5.0.

DETAILED DESCRIPTION OF THE INVENTION

The compositions of the present invention contain essential components as well as various nonessential components as indicated below.

ESSENTIAL COMPONENTS

Aloe Vera

The first essential component of the present invention is an aloe vera component having anthraquinone levels of no more than about 1%. The aloe vera component herein is derived from the leaves of Aloe vera Linne' which is the source of both aloe vera gel and aloe vera latex. These two products differ both chemically and therapeutically. Aloe vera gel is a clear, thin, gelatinous material obtained by crushing the parenchymal tissue found in the inner leaf tissue. Aloe latex is that material obtained from the dried latex of the aloe vera leaf. Aloe latex (or juice) has for centuries been used as a potent cathartic. Aloe vera gel is prepared from the leaf by various procedures, all of which involve its separation not only from the inner cellular debris, but, especially, from the specialized pericyclic tubules which lie just beneath the leaf epidermis or find. A more detailed discussion of these procedures can be found in U.S. Pat. No. 4,735,935 to McAnalley, issued Apr. 5, 1988; U.S. Pat. No. 4,178,372 to Coats, issued Dec. 11, 1979; and U.S. Pat. No. 3,892,853 to Cobble, issued Jul. 1, 1975; all of which are herein incorporated by reference. A still further discussion can be found in D. L. Smothers, *Drug & Cosmetic Industry*, 132(1): 40, 77–80, 1983. Present in the gel is a polysaccharide glucomannan, similar to guar gum, believed to account for the gel's emollient effect. Additionally, since the gel is separated from the latex pericyclic tubules, it is substantially free of anthraquinone glycosides, the cathartic actives of aloe latex. The aloe vera component suitable for use in the present invention contains anthraquinone levels of no more than about 1%, preferably no more than about 0.5%, and is available in a variety of forms. Such forms include aloe vera gel, aloe vera gel decolorized, aloe vera gel thickened, aloe vera gel concentrate (10:1), decolorized aloe vera gel concentrate (10:1), aloe vera spray dried powder (100:1) and aloe vera freeze dried powder (200:1). Alternatively, the compositions of the present invention may incorporate decolorized aloe vera whole leaf (1:1, 2:1 or 4:1) having anthraquinone levels of no more than about 1%, preferably no more than about 0.5%. However, preferred for use in the compositions of the present invention is aloe vera gel, the aloe vera freeze dried powder or the aloe vera spray dried powder, more preferably the aloe vera freeze dried powder or the aloe vera spray dried powder. Suitable aloe vera gels or decolorized aloe vera products can be obtained from Aloecorp (Harlingen, Tex.). The aloe vera component can be incorporated in the compositions of the present invention preferably at a weight ratio of pharmaceutical active to aloe vera component of at least about 1.5:1, more preferably at a weight ratio of pharmaceutical active to aloe vera component of at least about 1.7:1.

Pharmaceutical Actives

Pharmaceutically acceptable actives. Pharmaceutically acceptable actives which have an unpleasant taste which are useful in the present invention include actives selected from among the various groups of chemical compounds or materials suitable for oral administration and having a pharmacological action. Mixtures of various pharmaceutical actives may also be used. These pharmaceutically acceptable actives should be compatible with the other essential ingredients and compatible in combination with other included active materials or compounds and can be present at a level of from about 0.01% to about 90%, preferably from about 0.1% to about 75%, more preferably from about 1.0% to about 50% and most preferably from about 1.0% to about 25%. Suitable pharmaceutically acceptable active materials or compounds may be selected from, but are not limited to: bronchodilators, anorexiants, antihistamines, nutritional supplements (such as vitamins, minerals, fatty acids, amino acids, and the like), laxatives, analgesics, antacids, $H_2$-receptor antagonists, antidiarrheals, decongestants, antitussives, antinauseants, antimicrobials, antifungals, antivitals, expectorants, anti-inflammatory agents, antipyretics, their pharmaceutically acceptable salts and mixtures thereof.

The term "pharmaceutically acceptable salts" refers to salts prepared from pharmaceutically acceptable non-toxic bases including, but not limited to: inorganic bases and organic bases. Salts derived from inorganic bases include sodium, potassium, lithium, ammonia, calcium, magnesium, ferrous, zinc, manganous, aluminum, ferric, manganic salts and the like. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like.

Examples of decongestants useful in the compositions of the present invention include pseudoephedrine, phenylpropanolamine, phenylephrine and ephedrine, their pharmaceutically acceptable salts, and mixtures thereof.

Examples of antitussives useful in the compositions of the present invention include dextromethorphan, chlopedianol, carbetapentane, caramiphen, noscapine, diphenhydramine, codeine, hydrocodone, hydromorphone, their pharmaceutically acceptable salts, and mixtures thereof.

Examples of expectorants (also known as mucolytic agents) useful in the present invention include: guaifenesin, terpin hydrate, ammonium chloride, N-acetylcysteine, and ambroxol, their pharmaceutically acceptable salts, and mixtures thereof.

Examples of analgesics useful in the present invention include; morphine, codeine, meperidine, pentazocine, propoxyphene, acetaminophen, allopurinol, acetylsalicylic acid, choline salicylate, ketoprofen, magnesium silicate, fenoprofen, ibuprofen, flurbiprofen, indomethacin, naproxen, and many others and their pharmaceutically acceptable salts and mixtures thereof.

Examples of antihistamines useful in the present invention include; brompheniramine, chlorpheniramine, clemastine, dexchlorpheniramine, diphenhydramine, doxylamine, promethazine, terfenadine, triprolidine and many others and their pharmaceutically acceptable salts and mixtures thereof.

Analgesics, decongestants, antihistamines, expectorants and antitussives, as well as their acceptable dosage ranges are described in U.S. Pat. No. 4,783,465 to Sunshine et al., issued Nov. 8, 1988, and U.S. Pat. No. 4,619,934 to Sunshine et al., issued Oct. 28, 1986, which are incorporated by reference herein.

Examples of gastrointestinal agents suitable for use in the present invention include anticholinergics, including atropine, clidinium and dicyclomine; antacids, including aluminum hydroxide, bismuth subsalicylate, calcium carbonate and magaldrate; $H_2$-receptor antagonists including: cimetidine, famotidine, nizatidine and ranitidine; laxatives, including: phenolphthalein and casanthrol; and antidiarrheals including: diphenoxylate and loperamide.

Further examples of suitable analgesics, decongestants, antitussives, expectorants and antihistamines as well as bronchodilators, anorexiants, laxatives, antiemetics, antimicrobials, antibacterials, antifungals, anti-inflammatory agents, antivirals, antipyretics, nutritional supplements, anticholinergics, antacids, $H_2$-receptor antagonists, antidiarrheals and other miscellaneous gastrointestinal compounds and their acceptable dosage ranges are described in *Remington's Pharmaceutical Sciences*, pp. 734–789, 791–799, 861–868, 907–945, 875–888, 1002–1034, 1098–1121, 1124–1131, 1173–1224, 1232–1241 (Alfonso R. Gennaro, editor) (18th ed. 1990), herein incorporated by reference.

Pharmaceutically Acceptable Carrier

Various oral dosage forms can be used, including such solid forms as tablets, chewables, granules, lozenges and bulk powders and liquid forms such as syrups and suspensions. These oral forms comprise a safe and effective amount, usually at least about 0.1% of the aloe vera and active component. Solid oral dosage forms preferably contain from about 5% to about 95%, more preferably from about 10% to about 95%, and most preferably from about 25% to about 95% of the active component. Liquid oral dosage forms preferably contain from about 0.1% to about 50% and more preferably from about 1% to about 25% and most preferably from about 3% to about 10% of the aloe vera and active component.

Tablets can be compressed, tablet triturates, or multiple compressed, containing suitable binders, lubricants, diluents, disintegrating agents, coloring agents, flavoring agents, preservatives and flow-inducing agents.

Liquid oral dosage forms include aqueous and nonaqueous solutions, emulsions, suspensions, and solutions and/or suspensions reconstituted from noneffervescent granules, containing suitable solvents, preservatives, emulsifying agents, suspending agents, diluents, sweeteners, coloring agents, and flavoring agents. Specific examples of pharmaceutically acceptable carriers and excipients that may be used to formulate oral dosage forms, are described in U.S. Pat. No. 3,903,297, Robert, issued Sep. 2, 1975, incorporated by reference herein. Techniques and compositions for making solid oral dosage forms are described in Marshall, "Solid Oral Dosage Forms," *Modern Pharmaceutics, Vol. 7* (Banker and Rhodes, editors), 359–427 (1979), incorporated by reference herein. Techniques and compositions for making tablets (compressed and molded) and pills are described in *Remington's Pharmaceutical Sciences,* (Arthur Osol, editor), 1553–1593 (1980), incorporated herein by reference.

In preparing the liquid oral dosage forms, the aloe vera and active component is incorporated into an aqueous-based orally acceptable pharmaceutical carrier consistent with conventional pharmaceutical practices. An "aqueous-based orally acceptable pharmaceutical carrier" is one wherein the entire or predominant solvent content is water. Typical carriers include simple aqueous solutions, syrups, dispersions and suspensions, and aqueous based emulsions such as the oil-in-water type. The most preferred carrier is a suspension of the pharmaceutical composition in an aqueous vehicle containing a suitable suspending agent. Suitable suspending agents include Avicel RC-591 (a microcrystalline cellulose/sodium carboxymethyl cellulose mixture available from FMC), guar gum and the like. Such suspending agents are well known to those skilled in the art. While the amount of water in the compositions of this invention can vary over quite a wide range depending upon the total weight and volume of the aloe vera and active component and other optional non-active ingredients, the total water content, based on the weight of the final composition, will generally range from about 20 to about 75%, and, preferably, from about 20 to about 40%, by weight/volume. Methods for preparations and manufacture of solutions, suspensions, and emulsions are discussed in *Remington's Pharmaceutical Sciences* (Alfonso R. Gennaro, editor 18th ed.), pp 1519–1544, herein incorporated by reference.

Although water itself may make up the entire carrier, typical liquid formulations preferably contain a co-solvent, for example, propylene glycol, glycerin, sorbitol solution and the like, to assist solubilization and incorporation of water-insoluble ingredients, such as flavoring oils and the like into the composition. In general, therefore, the compositions of this invention preferably contain from about 5 to about 25 volume/volume percent and, most preferably, from about 10 to about 20 volume/volume percent, of the co-solvent.

The compositions of the present invention may also be incorporated into rapidly dissolving carriers or dosage forms. Suitable rapidly dissolving carriers can incorporate effervescent or other water-dispersible substances which, when dried, rapidly disintegrate upon coming into contact with an aqueous liquid. Suitable effervescent technology is described in U.S. Pat. No. 5,178,878, Jan. 12, 1993, to Wehling et al and in further detail in Chapter 6 of *Pharmaceutical Dosage Forms: Tablets,* Vol. I, $2^{nd}$ ed., A Lieberman ed., 1989, Marcel Dekker, Inc.; both of which are herein incorporated by reference.

Similarly, rapid dissolution may be achieved by incorporating the aloe vera and active mixture into a freeze dried form. Freeze-drying or lyophilization facilitates disintegration of the composition by forming the dried composition into an open matrix network. In most cases, this results in rapid permeation by the aqueous media, promoting timely delivery of the product's active ingredients. Suitable methods of freeze drying are well known in the art and commonly employed. Any suitable conventional method of freeze-drying may be utilized. A preferable method of freezing and drying is to fast freeze the composition and then dry the composition to a final moisture content of about 2% to about 5%. Suitable methods of freeze-drying and production are taught by U.S. Pat. No. 4,642,903, Feb. 17, 1987, to Davies, U.S. Pat. No. 4,946,684, Aug. 7, 1990, to Blank et al., U.S. Pat. Nos. 4,305,502 and 4,371,516, issued Dec. 15, 1981 and Feb. 1, 1983 respectively, to 6regory et al., and U.S. Pat. No. 5,188,825, Feb. 23, 1993, to Iles et al.; which are all incorporated herein by reference.

Alternatively, the compositions of the present invention may be vacuum dried. Vacuum drying involves at least the partial drying of compositions at temperatures above compositions' collapse temperature. Freeze drying, on the other hand, involves the drying of compositions at temperatures below the compositions; collapse temperature. Any suitable method of vacuum drying may be used. Suitable vacuum drying processes are described in U.S. Pat. No. 5,298,261, to Pebley et al., issued Mar. 29, 1994, herein incorporated by reference.

One other form of fast dissolving technology that may be applicable to the present invention is a liquid/liquid extract developed by Janssen Pharmaceutica Inc. and is identified by the trade name Quicksolv™. This technology is fully described in U.S. Pat. No. 5,215,756 herein incorporated by reference.

NONESSENTIAL COMPONENTS

Persons skilled in the art will quickly realize many other ingredients will be suitable for inclusion into the present invention. Nonessential components include, but are not limited to: coloring agents; flavoring agents, including: vanilla, cherry, grape, cranberry, orange, peppermint, spearmint, anise, blueberry raspberry, banana, chocolate, caramel, strawberry, lemon, lime, menthol and Prosweet™ MM50 (a combination of natural and artificial flavors and propylene glycol, available from Virginia Dare Extract Co., Inc., Brooklyn, N.Y.); sweeteners, including saccharin, dextrose, levulose, sucrose, fructose, cyclamate, mannitol, aspartame, and acesulfame K, along with many others; suspending agents, including xanthum gum, acacia gum, carboxymethylcellulose, starch and methylcellulose; preservatives; releasing agents, including polysorbate 80, sodium lauryl sulfate, vegetable oils and magnesium stearate; and water.

Another preferred nonessential component of the present invention is a cooling agent or a combination of cooling agents. Suitable cooling agents are those described in U.S. Pat. No. 4,136,163, Jan. 23, 1979, to Watson et al., U.S. Pat. Nos. 4,032,661 and 4,230,688, Jun. 28, 1977 and Oct. 28, 1980, respectively, to Rowsell et al. and U.S. Pat. No. 5,266,592, Nov. 30, 1993 to Grub et al., all of which are herein incorporated by reference. Particularly preferred cooling agents include N-ethyl-p-menthane-3-carboxamide (WS-3 supplied by Sterling Organics) taught by the above incorporated U.S. Pat. No. 4,136,163 and N, 2,3-trimethyl-2-isopropylbutanamide which is commercially available as WS-23 from Wilkinson Sword Limited and taught by the above incorporated U.S. Pat. No. 4,230,688. Another particularly preferred cooling agent is 3-1-menthoxypropane 1,2-diol (TK- 10 supplied by Takasago Perfumery Co., Ltd., Tokyo, Japan). This material is described in detail in U.S. Pat. No. 4,459,425, Jul. 10, 1984 to Amano et al. and incorporated herein by reference.

EXAMPLES

The following examples further describe and demonstrate embodiments within the scope of the present invention. The examples are given solely for the purpose of illustration and are not to be construed as limitations of the present invention, as many variations are possible without departing from the spirit and scope of the invention.

EXAMPLE I

| | |
|---|---|
| magnesium stearate | 0.5000 |
| sorbitol, compressed | 52.570 |
| silicone dioxide[1] | 0.1000 |
| citric acid, anhydrous | 6.2500 |
| sodium bicarbonate | 18.750 |
| flavor, spray dried | 0.5000 |
| pseudoephedrine HCl | 12.000 |
| brompheniramine maleate | 0.8000 |
| aloe freeze-dried powder | 8.5300 |

[1]Available as Cab-o-sil from Cabot Corporation, Tuscola, Illinois.

In an appropriately sized container, with Lightnin™ mixer (model #TS2010 (or a high shear homogenizer set at 30 to 50 RPM)) mixing at approximately 250 to 1000 RPM, add the :following agents allowing each to dissolve before adding the next. Mix vigorously (250 to 1000 RPM) for 45 minutes. Dry mixture in 45° C. oven for 12 hours or until moisture is driven off. Grind dry mixture to particle size suitable for compressing.

Dry blend via conventional blending methods (e.g., V-blender) the compressible sorbitol, magnesium stearate, dextromethorphan HBr, silicone dioxide, citric acid anhydrous, pretreated sodium bicarbonate, .pseudoephedrine HCl, brompheniramine maleate, and aloe freeze-dried powder.

Using a conventional tablet press in a humidity controlled room (<25 % RH), press tablets to a tablet weight of 500 mg. Protect tablets from moisture by sealing in glass jars or in foil pouches or blisters. Administration of one to two tablets is the normal and customary dosage.

Substantially similar results are also obtained when the pharmaceutically acceptable active is replaced, in whole or in part, with a therapeutically equivalent amount of dextromethorphan, HBr, doxylamine succinate, phenylpropanolamine HCl, chlorpheniramine maleate, guaifenesin, triprolidine HCl, diphenhydramine HCl, dimenhydrinate, loperamide, simethicone, acetaminophen, acetylsalicylic acid, ibuprofen, fenbufen, fenoprofen, flurbiprofen, indomethacin, naproxen or mixtures thereof.

EXAMPLE II

A syrup of the present invention is prepared by sequentially dissolving each of the following ingredients with agitation in a stainless steel or glass mixing tank:

| Ingredients | Weight % |
|---|---|
| dextromethorphan HBr | 0.1323 |
| guaifenesin | 1.3230 |
| granular sugar | 53.9920 |
| tween 80 | 0.0198 |
| glycerin | 1.9850 |
| propylene glycol | 17.8650 |
| sodium citrate | 0.5181 |
| citric acid, anhydrous | 0.3355 |
| potassium sorbate | 0.0993 |
| aloe vera spray-dried powder | 0.7500 |
| water, purified | q.s. to 100 ml |

Examples III and IV represent additional syrup formulations of the present invention made by combining the following components using conventional mixing technology as described in Example II.

EXAMPLE III

| Ingredients | Weight % |
|---|---|
| acetaminophen | 3.3340 |
| doxylamine succinate | 0.0417 |
| pseudoephedrine HCl | 0.2000 |
| dextromethorphan HBr | 0.1000 |
| ethyl alcohol, 95% | 10.5263 |
| | (% v/v) |
| liquid sugar | 66.000 |
| citric acid, anhydrous | 0.2986 |
| glycerin | 5.0000 |
| propylene glycol | 15.000 |
| flavor | 0.3700 |
| artificial color | 0.0500 |
| aloe vera spray-dried powder | 2.4500 |
| water, purified | q.s. to 100 ml |

EXAMPLE IV

| Ingredients | Weight % |
|---|---|
| loperamide | 2.4400 |
| granular sugar | 54.1280 |
| tween 80 | 0.0199 |
| glycerin | 1.9999 |
| propylene glycol | 17.9100 |
| sodium citrate | 0.5194 |
| citric acid, anhydrous | 0.3363 |
| potassium sorbate | 0.0995 |
| aloe vera freeze-dried powder | 1.6300 |
| water, purified | q.s. to 100 ml |

What is claimed is:

1. A pharmaceutical composition suitable for oral administration comprising:

a) from about 0.1% to about 90% of at least one unpleasant tasting, pharmaceutical active;

b) an effective amount of an aloe vera component for taste masking the unpleasant tasting, pharmaceutical active; and c) an orally acceptable pharmaceutical carrier wherein the aloe vera component contains no more than about 1% anthraquinones and wherein the ratio of pharmaceutical active to aloe vera component is at least about 1.5:1.

2. A pharmaceutical composition according to claim 1, wherein the level of the aloe vera component is from about 0.01% to about 2% of the composition and is selected from the group consisting of aloe vera gel, decolorized aloe vera whole leaf and mixtures thereof.

3. A pharmaceutical composition according to claim 2 wherein the pharmaceutical active is selected from the group consisting of analgesics, decongestants, expectorants, antitussives, antihistamines, and gastrointestinal actives and mixtures thereof.

4. A pharmaceutical composition according to claim 3, wherein the pharmaceutical active is selected from the group of pharmaceutical actives consisting of acetaminophen, ibuprofen, naproxen, dextromethorphan, HBr, doxylamine succinate, pseudoephedrine HCl, phenylpropanolamine HCl, chlorpheniramine maleate, guaifenesin, triprolidine HCl, diphenhydramine HCl, and mixtures thereof.

5. A pharmaceutical composition according to claim 4, wherein the composition additionally contains one or more flavoring agents.

6. A pharmaceutical composition according to claim 5, wherein the composition additionally contain one or more sweetening agents.

7. A pharmaceutical composition according to claim 6, wherein the composition additionally contains one or more releasing agents.

8. A pharmaceutical composition according to claim 7, wherein the composition additionally contains one or more cooling agent.

9. A pharmaceutical composition according to claim 8, wherein the cooling agent is selected from the group consisting of: 3-1-menthoxypropane 1,2-diol, N-ethyl-p-menthane-3-carboxamide, N,2,3-trimethyl-2-isopropylbutanamide and mixtures thereof.

10. A pharmaceutical composition according to claim 9, wherein the sweetening agent is selected from the group consisting of sodium saccharin, aspartame, acesulfame k, monoammonium glycyrrhizate, sucrose, mannitol and mixtures thereof.

11. A pharmaceutical composition according to claim 10, wherein the releasing agent is selected from the group consisting of: polysorbate 80, sodium lauryl sulfate, magnesium stearate and mixtures thereof.

12. A pharmaceutical composition according to claim 11, wherein the flavoring agent is selected from the group consisting of: menthol, peppermint, spearmint, raspberry, cranberry, cherry, orange, vanilla, anise, blueberry, banana, chocolate, caramel, strawberry, lemon, grape and mixtures thereof.

13. A pharmaceutical composition according to claim 12, wherein the pharmaceutical active is dextromethorphan and guaifenesin.

14. A method of treating allergy or allergy-like symptoms by administering to an individual having difficulty swallowing tablets or capsules a safe and effective amount of a composition according to claim 1.

15. A method of treating the symptoms of a gastrointestinal disorder by administering to an individual having difficulty swallowing tablets or capsules a safe and effective amount of a composition according to claim 1.

16. A method of treating the symptoms of a respiratory illness by administering to an individual having difficulty swallowing tablets or capsules a safe and effective amount of a composition according to claim 1.

* * * * *